United States Patent [19]

Piesche

[11] 4,057,755
[45] Nov. 8, 1977

[54] THERMAL CONDUCTIVITY DETECTOR CIRCUIT

[75] Inventor: Helfried Piesche, Owingen, Germany

[73] Assignee: Bodenseewerk Perkin-Elmer & Co., GmbH, Überlingen, Germany

[21] Appl. No.: 722,248

[22] Filed: Sept. 10, 1976

[51] Int. Cl.² .......................................... G01R 27/02
[52] U.S. Cl. .............................. 324/62; 324/DIG. 1; 73/362 AR; 318/674; 323/75 A; 323/75 N
[58] Field of Search ................... 324/62, DIG. 1; 323/75 A, 75 N; 73/362 AR; 318/663, 666, 674

[56] References Cited

U.S. PATENT DOCUMENTS

| 2,719,263 | 9/1955 | Flowers et al. | 324/62 |
| 2,974,279 | 3/1961 | Barry et al. | 324/62 |
| 3,161,821 | 12/1964 | Price et al. | 324/62 X |
| 3,287,978 | 11/1966 | Knudsen | 324/62 X |
| 3,379,973 | 4/1968 | Walton | 324/62 |
| 3,503,261 | 3/1970 | Riester et al. | 324/62 |
| 3,568,044 | 3/1971 | Elazar | 324/62 |
| 3,588,690 | 6/1971 | Griffin | 324/62 X |
| 3,859,594 | 1/1975 | Grindheim | 324/62 |

*Primary Examiner*—Stanley T. Krawczewicz
*Attorney, Agent, or Firm*—S. A. Giarratana; F. L. Masselle; J. D. Crane

[57] ABSTRACT

There is disclosed a circuit which supplements a bridge-type detector circuit in order to minimize non-linearities resulting in measurements of thermal conductivity by such type bridges. An auxiliary voltage source is described which has an adjustable output voltage which is servoed to follow the output voltage of a differential amplifier which is connected to the output of the bridge. When the bridge is balanced at the desired operating temperature, the auxiliary supply is switched in and this voltage now controls the current supplied to the bridge instead of the differential amplifier output voltage thus eliminating the cause of the non-linearities at the point of measurement.

6 Claims, 1 Drawing Figure

THERMAL CONDUCTIVITY DETECTOR CIRCUIT

BACKGROUND OF THE INVENTION

This invention relates generally to thermal conductivity detectors used in gas chromatography and more particularly to bridge type detectors.

Gas chromatographic separating columns utilize thermal conductivity detectors to determine the components of gas flowing therethrough. These detectors normally include a bridge circuit, driven by a constant-current source, which employs temperature-sensitive, heated filaments or thermistors having a positive temperature coefficient of resistance. One of these, or a pair of them, are placed in opposite legs of the bridge and are immersed in a reference or carrier gas flow of known thermal conductivity. A second one or pair, are placed in the remaining, opposite legs of the bridge and immersed in the gas flow at a point in the column after the introduction of the sample. The bridge output voltage is then dependent upon the difference in thermal conductivities between the reference gas and the sample gas to be measured, and the housing of the detector.

E.g., if the reference or carrier gas has a high thermal conductivity and the gas to be sampled a lower one, the latter causes the corresponding heated filaments to increase in temperature (and accordingly electrical resistance) relative to the reference filaments resulting in a bridge unbalance. This produces a proportional bridge output voltage which can be measured and recorded.

Although the sensitivity of the thermal conductivity detector increases with an increase in filament temperature, if it should rise too high, the filament will burn out.

One technique for preventing such overheating of the filament is disclosed in German AS No. 1,523,011. The supply voltage across the bridge circuit is tapped and compared with an adjustable reference voltage.

If the tapped voltage exceeds a predetermined limit, an overload protective circuit is activated which in turn controls the current output of the constant current supply so as to reduce the bridge circuit supply.

Another arrangement is disclosed in German OS No. 1,648,276. Here the measuring bridge is placed in the leg of another bridge circuit. The latter which is driven by a constant current source contains fixed resistors in the remaining legs thereof. When the bridge output voltage exceeds a given limit, corresponding to a given resistance change in the measuring bridge, an overload protective circuit again operates upon the constant current source to reduce the supply current fed to the bridge circuit.

Yet, another known technique employs a measuring bridge circuit, again, placed in one leg of a second bridge circuit. An adjustable resistor is placed in the opposite leg. By setting this resistor at a particular value representing a particular temperature for the filaments a balance point for the bridge is determined which occurs when the total resistance between the supply terminals of the measuring bridge equals the preset adjustable resistor.

The resistance of the measuring bridge depends on the heating of the filaments which in turn is a function of the current supplied thereto. When the bridge is unbalanced, the output voltage of the latter is supplied to the input of a differential amplifier. The output of the amplifier drives the base of a current control transistor which is connected between a power supply and the bridge supply point. The bridge supply current is thus varied to effect the necessary change in the measuring bridge resistance to balance the second bridge circuit.

With such an arrangement, the temperature of the sensing filaments can easily be preset and adapted to the varying requirements of individual applications. However, this arrangement has also been found to result in certain non-linearities in the measuring bridge circuit due to the fact that its resistance also changes when the filaments are exposed to the sample gas components. This causes an unbalance of the other bridge circuit which results in an altering of the current supplied. As a consequence, the measuring bridge circuit is accordingly affected with different currents depending on its own degree of unbalance.

It is therefore a primary object of this invention to provide a thermal conductivity detector circuit which will allow for presetting the filament temperature and still provide a linear reading when the measuring bridge becomes unbalanced due to the influence of the sample gas components on the filaments.

SUMMARY OF THE INVENTION

Toward the accomplishment of this and other objectives readily apparent from the following discussion and accompanying schematic, there is disclosed an improved thermal conductivity circuit including a measuring bridge circuit which is disposed in one leg of a second bridge circuit. The measuring bridge circuit comprises respective filaments which are immersed, for instance, in the reference and sample gas flows in a gas chromatographic separating column. An adjustable resistor is connected in the leg of the second bridge, oppositely disposed from the measuring bridge leg. A differential amplifier is connected to the output terminals of the second bridge and controls the flow of current through a control transistor. To avoid the non-linearities normally attributed to this type of bridge detector circuit, this invention provides for an auxiliary voltage supply, which is switched in to control the flow of current through the control transistor when the filaments in the measuring bridge circuit have reached the operating temperature set by the adjustable resistor. The auxiliary voltage source includes a second voltage supply which has an adjustable output and a means for comparing the output of the differential amplifier with the adjustable output of the second voltage supply. The comparing means drives the adjustable supply through a suitable servo control circuit, and when the supply output voltage equals the differential output voltage the servo loop is opened and the control transistor is disconnected from the differential amplifier output and connected to the adjustable voltage output. This interchange can be done manually or automatically. Thus the control current is fixed and becomes independent of other factors which cause the measuring bridge resistance to change, and, in turn, would otherwise result in non-linearities in the measurements made.

Figure 1 shows a schematic circuit diagram of the invention.

DESCRIPTION OF THE PREFERRED EMBODIMENT

Figure 1:
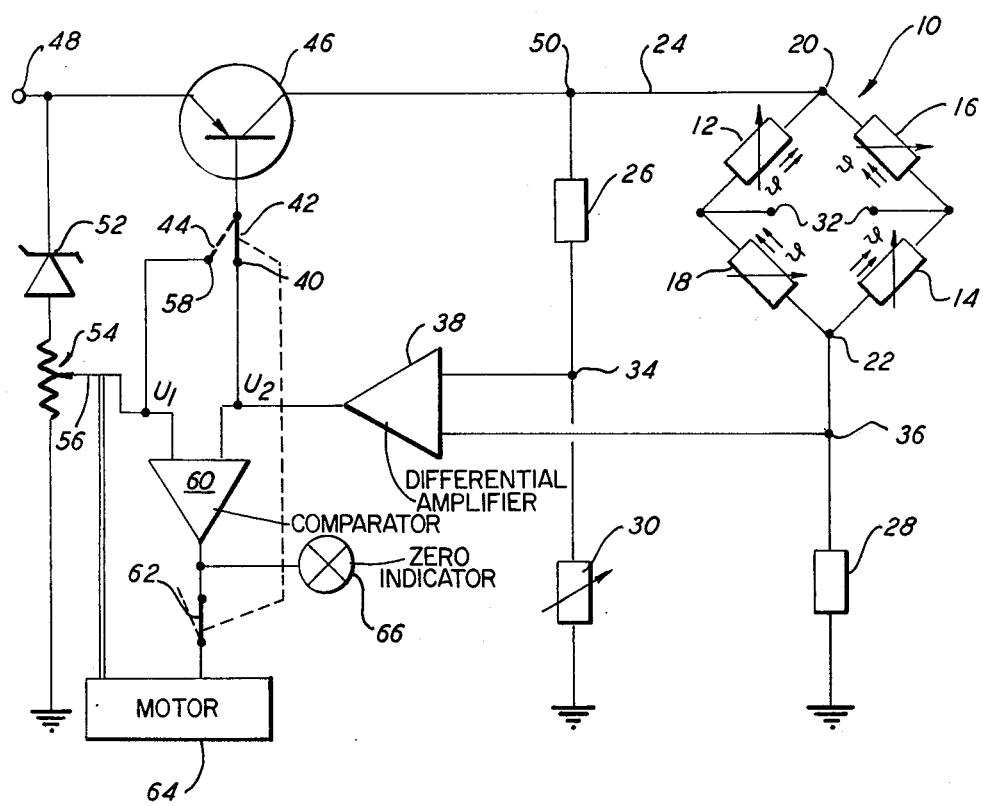

A measuring bridge circuit 10 includes a first pair of filaments 12 and 14, electrically connected in opposite legs. These are physically immersed in the channel of a gas chromatographic separating column through which the sample and carrier gas passes. Filaments 16 and 18 are connected in the opposite legs of the measuring bridge and are positioned in the reference gas stream in the separating column.

The supply terminals 20 and 22 of the measuring bridge 10 are connected in one leg of a second bridge 24. The measuring bridge output voltage appears at terminals 32 and is a measure of the bridge unbalance and therefore a measure of the concentration of the sample components in the gas stream to be analysed.

Connected in two of the oppositely disposed legs are fixed resistors 26 and 28, while a variable resistor 30 is electrically connected in the leg opposite the measuring bridge. The output of the second bridge 24 appears at terminals 34 and 36, which are connected to respective inputs of the differential amplifier 38.

The differential amplifier output is connected to contact 40 of switch 42. The contact arm 44 of the switch is connected to the base of control transistor 46, which is disposed between the voltage supply terminal 48 and the second bridge supply terminal 50. The other supply terminal of the second bridge is connected to ground.

An adjustable auxiliary voltage source is provided which comprises a zener diode 52, whose cathode is connected to terminal 48 and whose anode is connected to one end terminal of potentiometer 54. The other end of the potentiometer is connected to ground potential while the wiper 56 is electrically connected to contact 58 of switch 42. The wiper is likewise connected to input $U_1$ of comparator 60 while input $U_2$ is connected to contact 40 and the differential amplifier output.

The comparator output is connected through switch 62 to a servo control circuit and motor 64, which drives the wiper 56 whenever an unbalance appears between $U_1$ and $U_2$. Switch 62 is ganged to switch 42 such that it is in the closed position as shown when switch 42 is connected as shown, and in an open position when contact arm 44 is in the dashed position. The comparator output is also connected to a zero indicator 66 which gives a visual indication when $U_1$ and $U_2$ are balanced.

In operation, resistor 30 is set to a predetermined value which represents a desired operating temperature for the filaments. Switch 42 is in the position shown. The voltage at terminals 34 and 36, amplified by the differential amplifier 38, controls transistor 46 so as to provide a supply current to the bridge circuit 24, and in turn the measuring bridge circuit 10, such that eventually the filaments reach the desired temperature. At the same time comparator 60, in response to the unbalance between the differential amplifier output and the wiper voltage causes the wiper to be driven to a point where its voltage equals the differential amplifier output. The servo control circuit 64 will continuously drive the wiper to maintain the balance of the two voltages.

When the balance has been achieved, the comparator output reflects the balance via zero indicator 66 and the operator can manually switch the pole of 42 to the dashed position 44. Since switch 62 is ganged to switch 42 the former opens and the follow-up servo loop is deactivated so that wiper 56 remains at the balance position. Transistor 46 is now controlled by the voltage appearing at wiper 56.

Accordingly, a constant current proportional to the preset filament temperature is supplied to bridge circuit 24 and in turn, the measuring bridge circuit 10. With the supply current constant, the bridge circuit 10 operates in a linear mode so that the bridge output voltage at terminals 32 is proportional to the concentration of the sample gas components occurring at the position of the "sample" filaments.

Alternative embodiments of the auxiliary voltage supply and portions thereof will be readily apparent to those skilled in the art. E.g., the manual switching of switch 42, when the voltage at $U_1$ is balanced with the output of the differential amplifier can be effected automatically. For instance, a relay (not shown) normally energized by the voltage at the output of comparator 60 and having contacts implementing the functions of switches 42 and 62, would be released when the voltages at $U_1$ and $U_2$ became balanced.

Again, other alternatives to the embodiment described will be obvious to those skilled in the art and the breadth of the present invention should only be limited by the scope of the claims that follow.

What is claimed is:

1. In a thermal conductivity detector circuit including a measuring bridge having respective pairs of filaments electrically connected in corresponding legs of said bridge, said measuring bridge positioned in one leg of a second bridge circuit, an adjustable resistor electrically connected in the leg of said second bridge opposite the leg containing said measuring bridge circuit, a differential amplifier connected to the output terminals of said second bridge, current control means connected in circuit between a supply voltage source and said second bridge for supplying current to said second bridge, the output voltage of said differential amplifier controlling the flow of current through said current control means whereby said second bridge becomes balanced, wherein the improvement comprises an auxiliary voltage source for controlling said current control means including:
   a. a second voltage supply having an adjustable output voltage;
   b. means for electrically comparing the adjustable output voltage of said second supply to the output of said differential amplifier;
   c. means responsive to the output of said comparing means for varying the output voltage of said second voltage supply;
   d. means for disconnecting said differential amplifier output and electrically connecting said adjustable output voltage of said supply to said current control means when said adjustable output voltage equals the output voltage of said differential amplifier; and
   e. means for interrupting said means for varying the voltage supply when said adjustable output voltage equals the output of said differential amplifier.

2. The improved detector of claim 1 wherein said current control means includes a transistor connected in circuit between said supply voltage source and said second bridge circuit, and wherein the output of said differential amplifier is connected to the base of said transistor through a first switch means.

3. The improved detector of claim 2, wherein said voltage supply having an adjustable output comprises:
   a. a zener diode; and
   b. a potentiometer, including a wiper, electrically connected in series with said zener diode; said series connection of said zener diode and said potentiometer connected in parallel across said supply voltage source, said adjustable output voltage appearing at said wiper, said first switch means including a contact connected to said differential amplifier output, a contact connected to said wiper and a contact arm connected to said transistor base.

4. The improved detector of claim 3 wherein said means for comparing comprises a comparator having respective inputs connected to the output of said differential amplifier and to said wiper, and wherein said means for varying said second voltage supply includes a servo control circuit responsive to the electrical output of said comparator and adapted to vary the position of said wiper in response to said comparator output, and wherein said means for interrupting includes a second switch electrically connected in series with said servo control circuit, said second switch adapted to open the series connection in said servo control circuit when said first switch means disconnects said differential amplifier output and connects said wiper to said transistor base.

5. The improved detector of claim 4 further comprising a zero voltage indicator electrically connected to the output of said comparator.

6. The improved detector of claim 4 further comprising means electrically connected to the output of said comparator and adapted to automatically connect said contact arm to said wiper contact when said adjustable output voltage equals the output voltage of said differential amplifier.

* * * * *